(12) United States Patent
Keane

(10) Patent No.: US 10,617,506 B2
(45) Date of Patent: Apr. 14, 2020

(54) METHOD AND PROSTHESIS FOR PERCUTANEOUS HERNIA REPAIR

(71) Applicant: David Keane, Dublin (IE)

(72) Inventor: David Keane, Dublin (IE)

(*) Notice: Subject to any disclaimer, the term of this patent is extended or adjusted under 35 U.S.C. 154(b) by 393 days.

(21) Appl. No.: 15/340,107

(22) Filed: Nov. 1, 2016

(65) Prior Publication Data

US 2017/0042656 A1  Feb. 16, 2017

Related U.S. Application Data

(62) Division of application No. 14/009,632, filed as application No. PCT/IB2012/000820 on Apr. 11, 2012, now Pat. No. 9,510,926.

(60) Provisional application No. 61/474,023, filed on Apr. 11, 2011.

(51) Int. Cl.
| | |
|---|---|
| *A61F 2/02* | (2006.01) |
| *A61F 2/00* | (2006.01) |
| *A61B 17/00* | (2006.01) |
| *A61B 18/00* | (2006.01) |

(52) U.S. Cl.
CPC ........ *A61F 2/0063* (2013.01); *A61B 17/0057* (2013.01); *A61B 2017/00004* (2013.01); *A61B 2017/0061* (2013.01); *A61B 2017/0065* (2013.01); *A61B 2017/00469* (2013.01); *A61B 2017/00597* (2013.01); *A61B 2017/00606* (2013.01); *A61B 2017/00615* (2013.01); *A61B 2017/00623* (2013.01); *A61B 2018/00339* (2013.01); *A61B 2018/00577* (2013.01); *A61F 2002/0072* (2013.01); *A61F 2210/0085* (2013.01)

(58) Field of Classification Search
CPC .. A61F 2/00; A61F 2/0063; A61F 2/02; A61F 2002/30062; A61F 2210/0085; A61F 2210/0004; A61B 17/0057; A61B 2017/00597; A61B 2017/00606; A61B 2017/0061; A61L 27/3604; A61L 27/3687
See application file for complete search history.

(56) References Cited

U.S. PATENT DOCUMENTS

| | | | | |
|---|---|---|---|---|
| 5,545,178 | A * | 8/1996 | Kensey | A61B 17/0057 604/15 |
| 2004/0087980 | A1 | 5/2004 | Ford et al. | |
| 2010/0168651 | A1* | 7/2010 | Kassab | A61M 25/0147 604/28 |

* cited by examiner

*Primary Examiner* — Vi X Nguyen
(74) *Attorney, Agent, or Firm* — Burns & Levinson, LLP; Bruce D. Jobse

(57) ABSTRACT

A method and prosthesis is provided for percutaneous repair of an anatomical defect, such as an inguinal hernia. The method involves percutaneously accessing the inguinal canal of a patient. Following hernia reduction, if required, the hernia defect may be accessed and repaired percutaneously from within the inguinal canal. An implantable prosthesis may be percutaneously delivered into the inguinal canal. The prosthesis may be advanced along the inguinal canal from the percutaneous entry location to the defect site, where it may be deployed over and/or within the defect. A biocompatible foam material may be percutaneously delivered into the inguinal canal to reduce and/or repair the hernia defect. The foam may fill and solidify in the canal to prevent abdominal viscera from reentering the canal. Ablative therapy may be performed within the inguinal canal to cause a fibrotic response resulting in scar tissue formation and/or tissue shrinkage that narrows the canal.

15 Claims, 11 Drawing Sheets

METHOD AND PROSTHESIS FOR PERCUTANEOUS HERNIA REPAIR

CROSS-REFERENCE TO RELATED APPLICATIONS

This application is a divisional of U.S. application Ser. No. 14/009,632, filed on Feb. 13, 2014, which is a 371 U.S. National Stage Application of International Application No. PCT/IB2012/000820, filed on Apr. 11, 2012, which claims the benefit of U.S. Provisional Application Ser. No. 61/474,023, filed on Apr. 11, 2011, each of which is herein incorporated by reference in its entirety.

FIELD

The present invention relates to a method and implantable prosthesis for percutaneous hernia repair.

BACKGROUND

Various techniques are known for repairing tissue and muscle wall defects, including hernia defects such as inguinal and ventral hernias. Such repair procedures typically employ open surgical or laparoscopic techniques. A hernia repair may involve the use of an implantable prosthesis, such as a mesh plug and/or patch, that is employed to plug and/or cover the defect.

SUMMARY

The present invention relates to a method and/or prosthesis for percutaneous repair of an anatomical defect, such as a tissue or muscle wall defect. The method and/or prosthesis may have particular application for percutaneous repair of an inguinal hernia defect.

In one embodiment, a method involves percutaneously accessing an inguinal canal of a patient. Following reduction of the hernia, if required, the hernia defect may be accessed and repaired percutaneously from within the inguinal canal.

According to one aspect, the method may involve percutaneously delivering an implantable prosthesis into the inguinal canal. The prosthesis may be advanced along the inguinal canal from the location of the percutaneous entry toward the defect, and placed at the defect.

According to another aspect, the method may involve percutaneously delivering a biocompatible foam material into the inguinal canal.

According to a further aspect, the method may involve percutaneously performing ablative therapy within the inguinal canal sufficient to cause a fibrotic response that results in scar tissue formation and/or tissue shrinkage that narrows the canal.

The method of percutaneously repairing the hernia defect may involve any one or combination of an implantable prosthesis to plug and/or cover the defect, a biocompatible material to fill the inguinal canal, and ablation therapy to produce tissue scar formation and/or tissue shrinkage in the inguinal canal.

BRIEF DESCRIPTION OF DRAWINGS

Various embodiments of the invention will now be described, by way of example, with reference to the accompanying drawings, in which.

DETAILED DESCRIPTION

Figure 1:
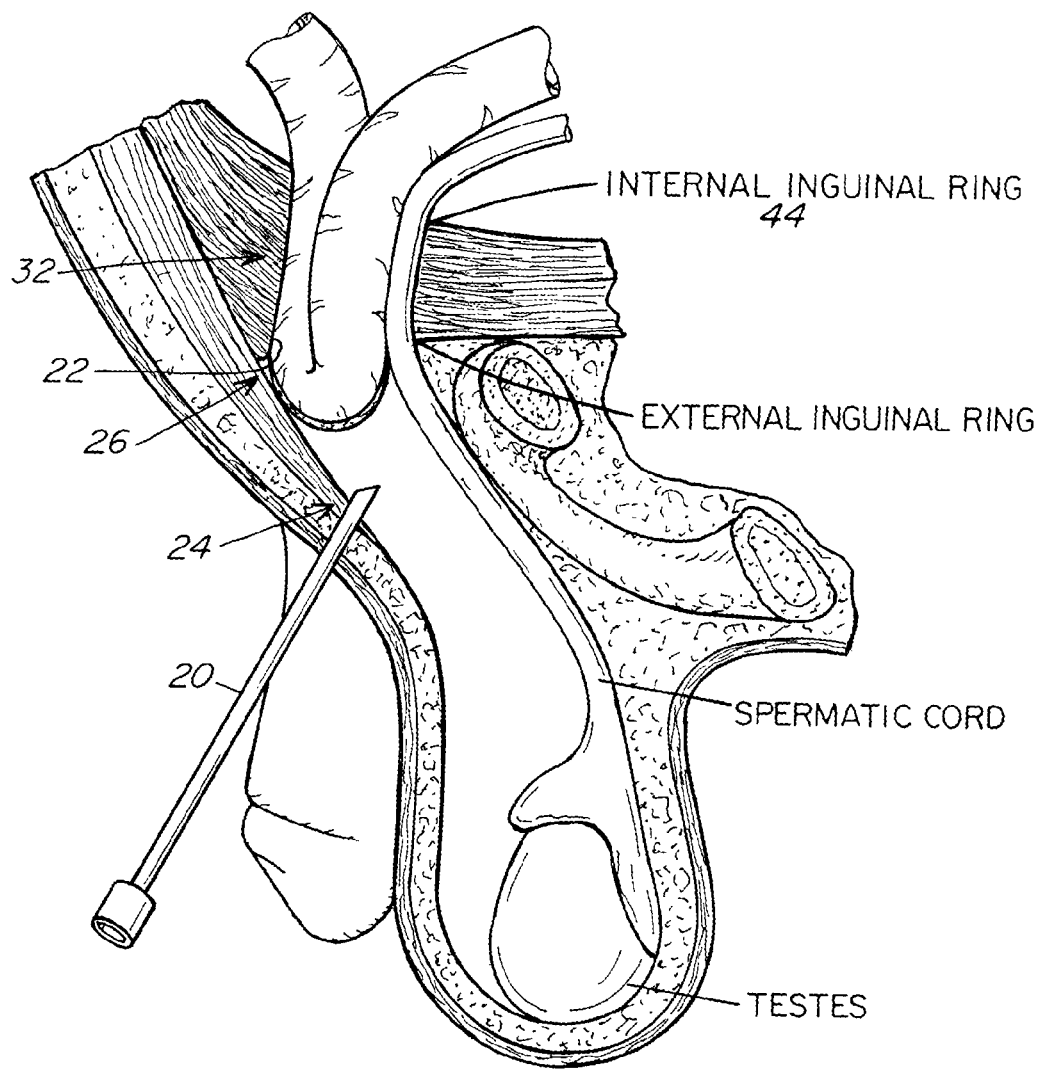
FIGS. 1-8 are schematic illustrations of a method of percutaneously repairing an inguinal hernia according to one embodiment of the invention.

A method and an implantable prosthesis are provided for percutaneously repairing an anatomical defect, such as a tissue or muscle wall defect. The procedure and device may be particularly suited for repairing an inguinal hernia by providing percutaneous access through a patient's skin and into the inguinal canal to repair the hernia defect. In this manner, the procedure may be performed without having to make a surgical incision into the patient.

Percutaneous access to the defect site, such as the inguinal canal, may be accomplished using a needle, a guidewire, and a sheath. More particularly, the needle may be percutaneously introduced through the skin and into the inguinal canal, followed by the introduction of the guidewire through the needle. The needle is thereafter removed and the sheath is subsequently introduced over the guidewire into the inguinal canal. If desired, a dilator may be employed to facilitate introduction of the sheath. After placement of the sheath, the guidewire, and the dilator if used, may be removed with the sheath remaining in place to provide direct percutaneous access to the inguinal canal, or other defect site, for repairing the defect. In this regard, the method involves use of a Seldinger-like technique to percutaneously access the inguinal canal.

Once access to the inguinal canal has been established, the hernia may be reduced, if necessary. Reduction of the hernia may be accomplished using one or more techniques including, but not limited to, insertion of a finger through the sheath, injection of a foam, gel or fluid, such as gas or liquid, through the sheath, and/or the introduction of a surgical tool, such as a surgical balloon, to push the hernia from the inguinal canal. With the contents of the inguinal canal reduced, repair of the hernia defect may be carried out percutaneously through the sheath.

The hernia defect may be repaired with an implantable prosthesis that is introduced into the inguinal canal, or other defect site, through the sheath. Once introduced, the prosthesis may be advanced from the percutaneous access location and along the canal to the site of the defect, where it may then be placed over, into or through the defect.

The prosthesis may include a plug and/or patch configured to be placed into and/or over the defect. The prosthesis may be collapsible or compressible to a reduced or slender configuration for passage through the sheath. The prosthesis may be expandable to an open, deployed or expanded configuration for plugging, capping or covering the defect. The prosthesis may include one or more features to facilitate deployment and/or expansion.

The prosthesis may include a distal patch that is advanced from the inguinal canal through and beyond the hernia defect in a collapsed configuration. The patch may thereafter be opened or expanded so that is can be deployed over the defect. Once expanded, the patch may be retracted back and positioned against the distal or posterior surface of the abdominal wall to cover the defect. For repairing an indirect inguinal hernia, the patch may be advanced through and deployed over the inguinal ring.

Once deployed, it may be desirable to anchor or secure the patch in position over the defect. The prosthesis may include an elongated tether or cord that is attached to and extends from the patch. The cord may be pulled and/or tensioned to hold the patch in position against the abdominal wall. An end of the cord opposite the patch may be anchored proximally to maintain the patch against the wall at the hernia defect. The prosthesis may include a proximal anchor that is to be attached to the cord to anchor the patch. The proximal anchor may be configured for subcutaneous placement. The patch may include one or more features, such as projections, hooks, barbs or anchors, that extend from one or more regions of the patch to grip tissue adjacent the hernia defect and stabilize the patch in position.

The distal patch may employ any configuration suitable for the anatomical region of the hernia defect. In one embodiment, the patch may have an oval shape for covering the internal inguinal ring, although other configurations are contemplated. The patch may include one or more features for accommodating anatomical features or sensitive structures occupying the repair site. In one embodiment, the patch may include an indentation, notch or other relief along its periphery for accommodating inguinal nerves and/or the spermatic cord.

For some repair procedures, a biocompatible foam material may be introduced into the inguinal canal to reduce and/or repair the hernia defect. The foam may be injected into the canal to reduce the hernia and solidify in the canal. The foam may permanently or temporarily fill the canal to prevent abdominal viscera from reentering the canal. The foam may solidify to fill the three-dimensional shape of the canal and thereby resist upward migration into the abdomen. The foam may be formed of any suitable non-absorbable material or absorbable material, such as collagen, as should be apparent to one of skill in the art. If desired, the foam may be formed of a radiopaque material.

For an indirect inguinal hernia, foam may be injected until the canal is filled to the internal inguinal ring. If desired, the foam may be capped or covered distal to the internal inguinal ring using either a permanent or temporary cap or patch. In one embodiment, the foam may be used in conjunction with the distal patch and the proximal anchor, whereby the foam is located between the patch and the anchor. In another embodiment, the foam may be capped using a distal patch that is positioned over the internal inguinal ring.

For some inguinal hernia repair procedures, reduction of the hernia may be followed by ablative therapy within the inguinal canal that is sufficient to cause a fibrotic response resulting in scar tissue formation and/or tissue shrinkage that narrows the canal. The ablative therapy may involve full or partial circumferential ablation of the canal. If desired, tissue ablation may extend circumferentially about a limited region of the canal to avoid ablation at regions of nerves or other sensitive structures within the canal. Ablation may be performed under direct visualization, such as by using a fiber optic device, to avoid damage to or ablation of nerves or other sensitive structures present in the inguinal canal. Ablation may be performed using any suitable ablative device as should be apparent to one of skill in the art.

Ablation may be performed in conjunction with an implantable prosthesis to plug and/or cover the defect in the inguinal canal. The prosthesis may include a distal plug and/or patch. If desired, the plug or patch may be held in position using a tether alone or together with a proximal anchor, such as described above.

The procedure may be carried out under a sterile technique using a local anesthesia and conscious sedation. An interventional radiologist or a minimally invasive surgeon may perform the procedure. The repair procedure may be performed under fluoroscopic or ultrasonic guidance, under internal light emission, or even without imaging.

One illustrative embodiment of a method for percutaneous repair of an inguinal hernia is described below in conjunction with FIGS. 1-10. It is to be appreciated, however, that one or more aspects of the method may be employed to percutaneously access and repair other anatomical defects as should be apparent to one of skill in the art.

As shown in FIG. 1, a needle 20 is percutaneously introduced into the inguinal canal 22, preferably using a sterile technique. As illustrated, the needle 20 may be introduced at a region 24 of the inguinal canal located laterally away from the hernia defect 26. Introduction of the needle may be carried out under a local anesthesia and conscious sedation, although other suitable anesthetic techniques are contemplated as should be apparent to one of skill in the art. In one embodiment, the inguinal canal is accessed with a hollow 16-gauge beveled needle. However, the inguinal canal may be accessed using any suitable needle or other device as should be apparent to one of skill in the art.

Figure 2:
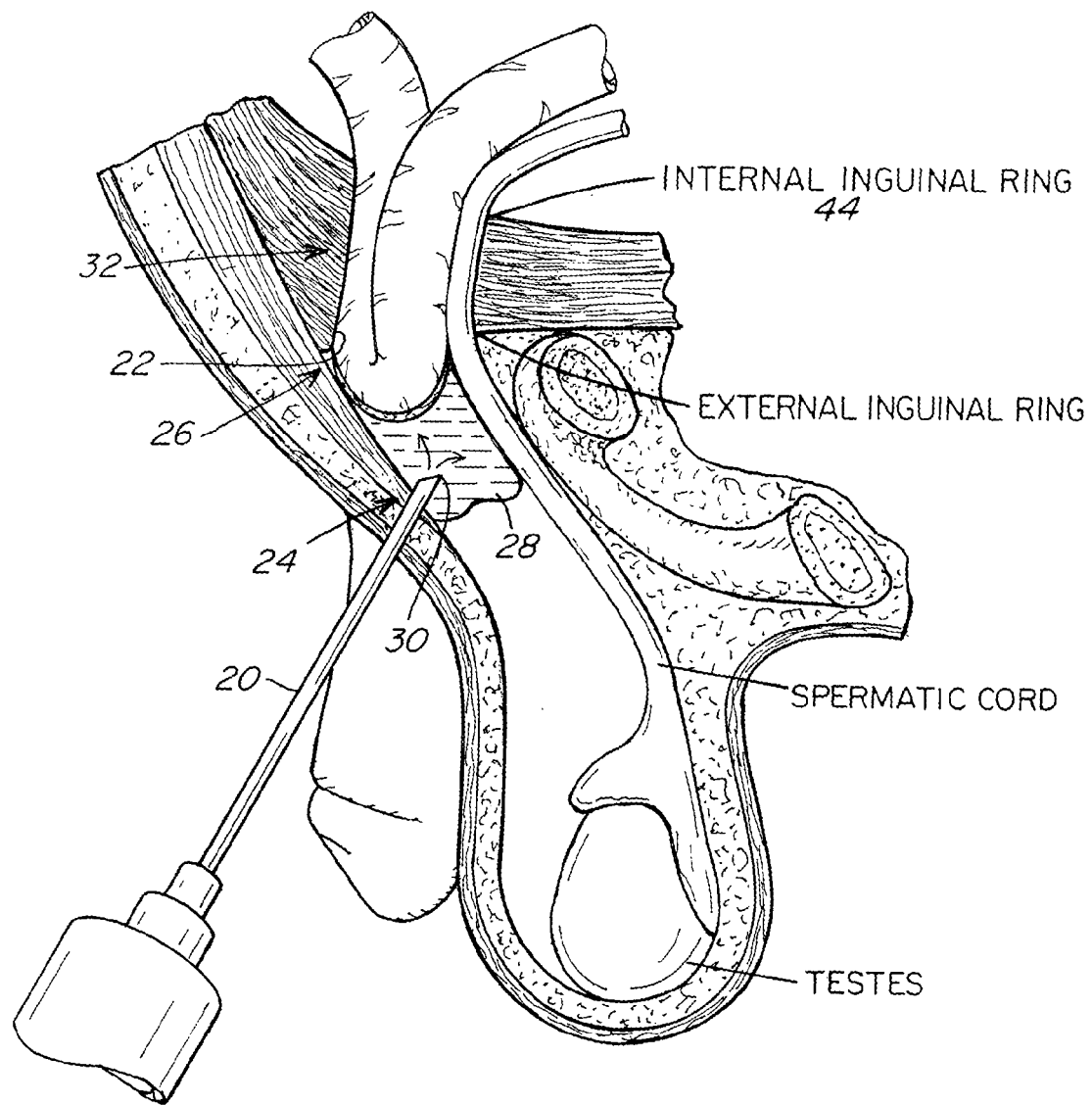

As shown in FIG. 2, a contrasting agent 28 may be injected through the needle 20 to confirm the anatomical location of the needle tip 30 within the inguinal canal 22. The contrast agent 28 may also be used to define the anatomical boundaries of the inguinal canal, including the location of the inguinal ring 32. The contrasting agent may be a radiographic contrast agent, such as a liquid or paste, that is injected through the needle under fluoroscopy in a manner known to one of skill in the art.

Figure 3:
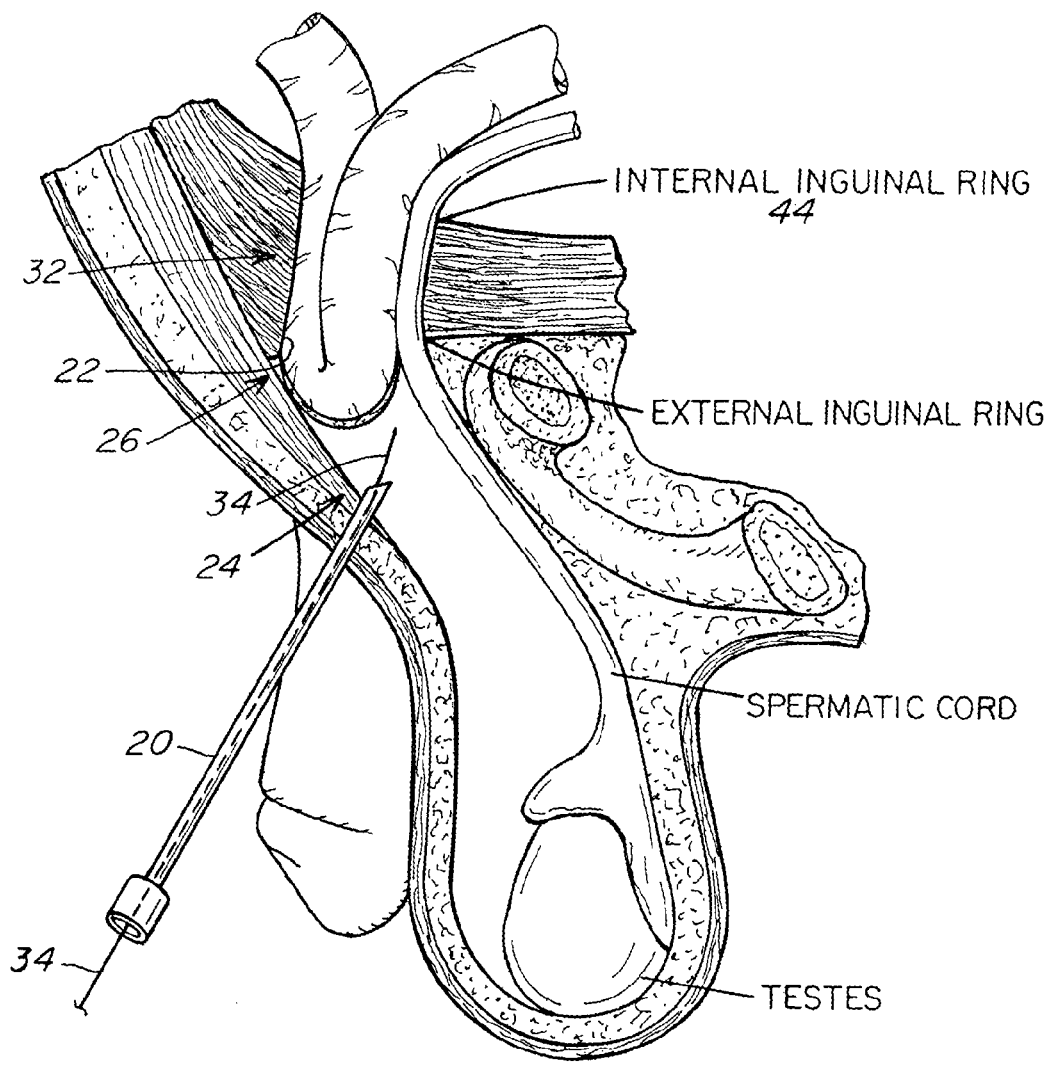
Figure 4:
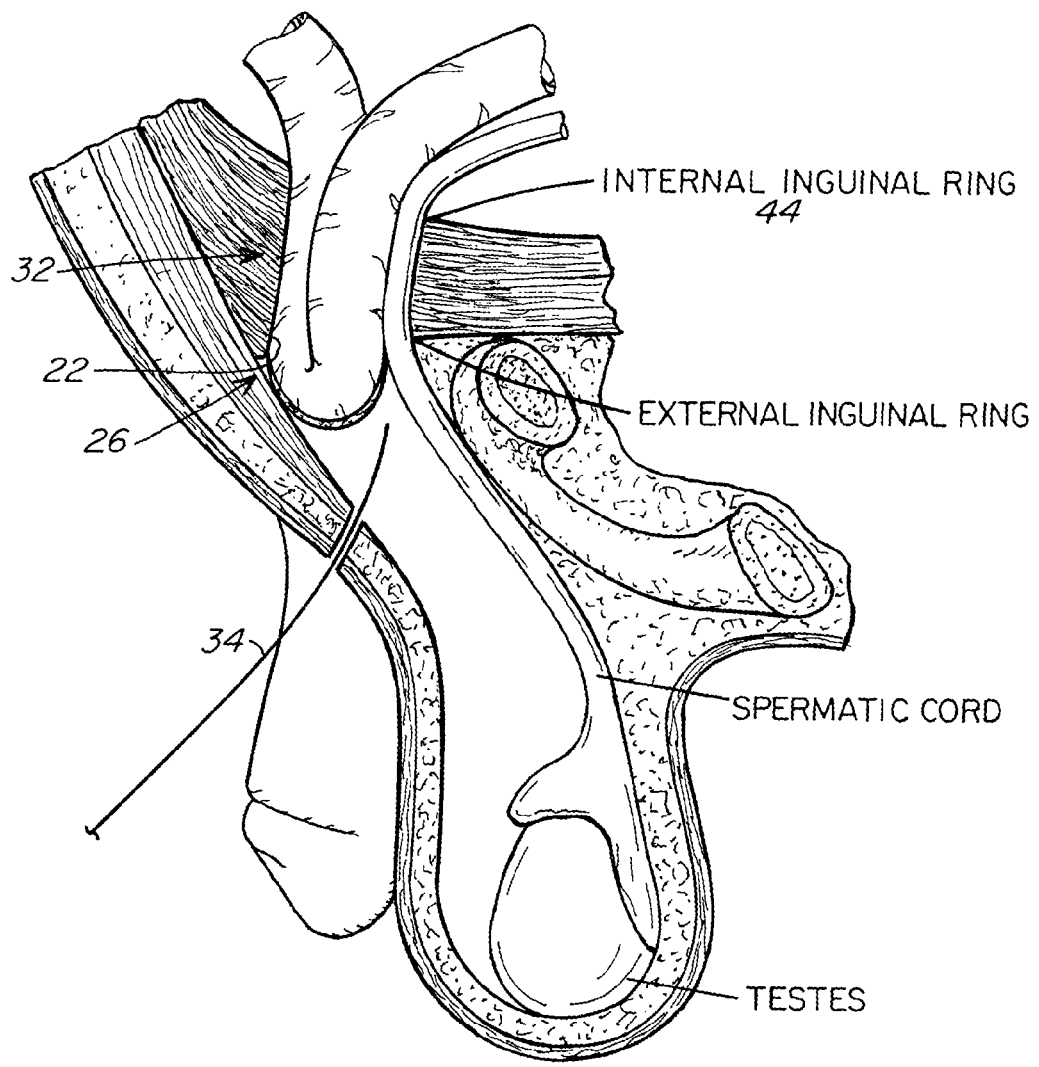

As shown in FIG. 3, a guidewire 34 or exchange wire may be introduced into the inguinal canal 22 through the needle 20, for example, under fluoroscopic guidance. As illustrated, the guidewire 34 may be extended along a portion of the canal in a lateral direction toward the inguinal ring 32. After the guidewire 34 has been positioned at its desired location, the needle is removed while maintaining the guidewire in the inguinal canal 22, as shown in FIG. 4.

Figure 5:
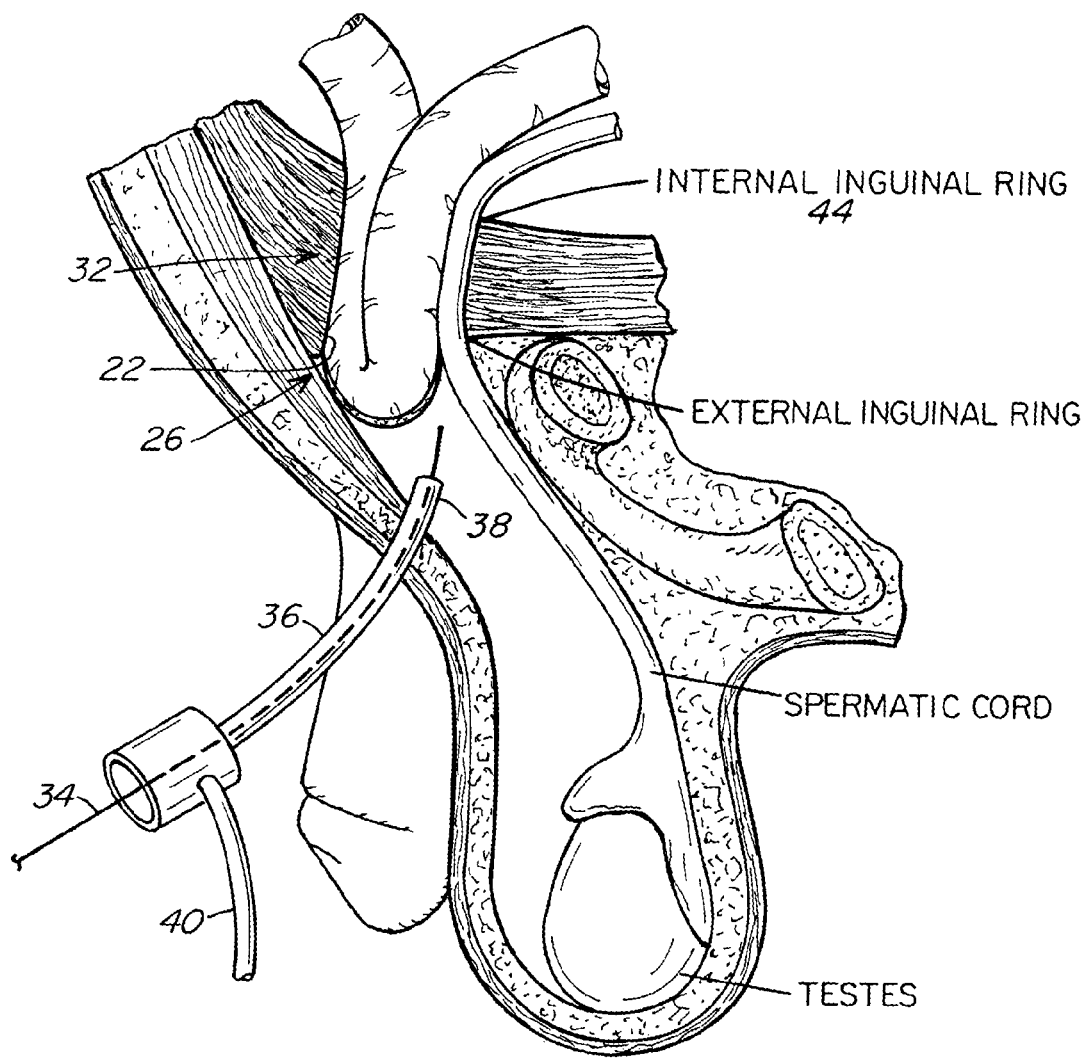
Figure 6:
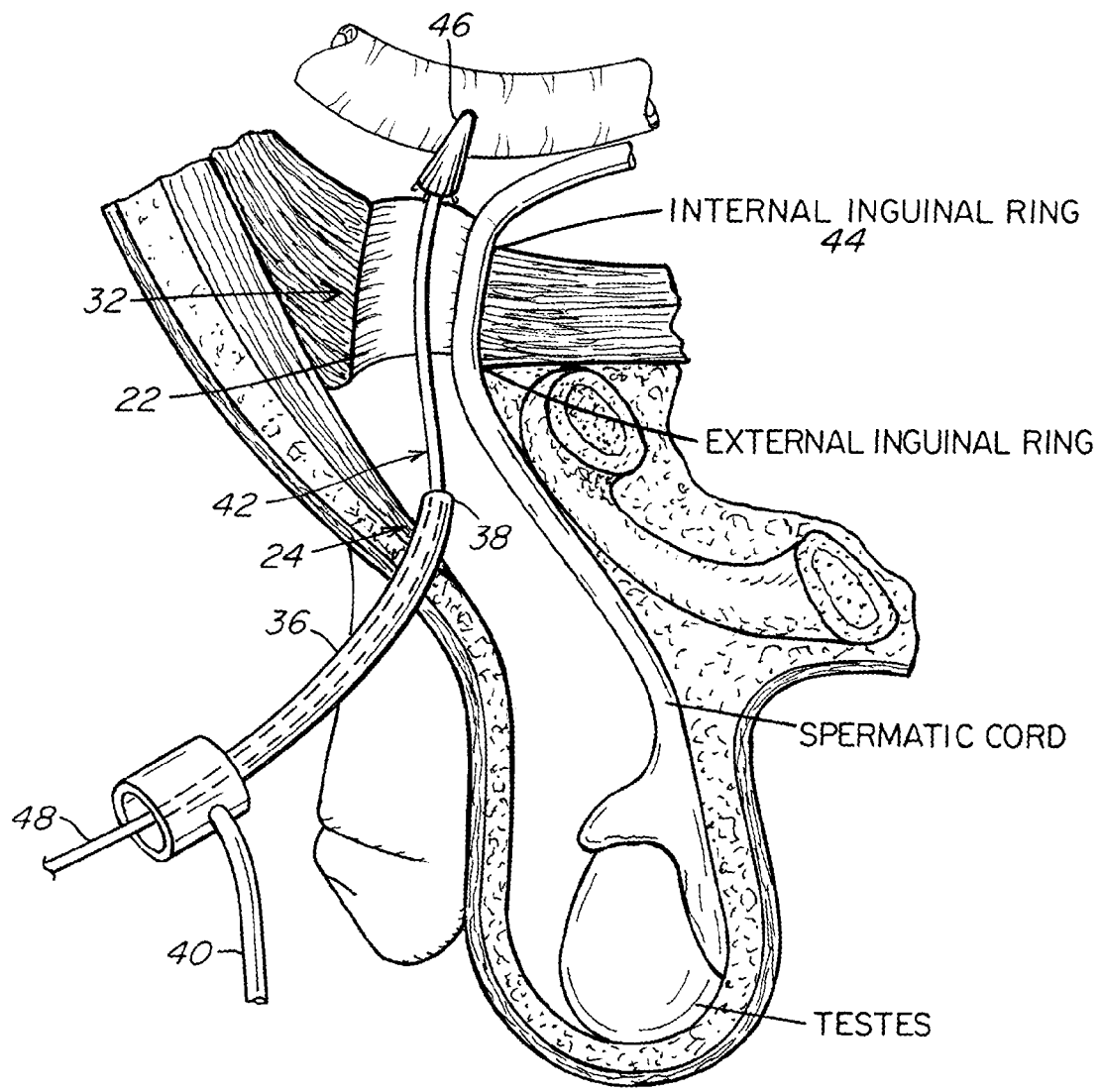

As shown in FIG. 5, an introducer sheath 36 may be introduced into the inguinal canal 22 over the guidewire 34. As illustrated, the tip 38 of the sheath 36 may be directed laterally (FIG. 6) in the canal towards the inguinal ring 32. The sheath 36 may include a side arm 40 that can be employed to inject additional contrast during the repair procedure to further delineate the anatomy, if desired. The side arm 40 may also be used to irrigate and aspirate the site, and inject a prophylactic antibiotic solution into the site, if desired, prior to removal of the sheath.

To facilitate the introduction of the sheath 36 into the canal, a dilator may be used in conjunction with the sheath in a manner as should be apparent to one of skill in the art. In one embodiment, a balloon dilator may be advanced along the guidewire prior to the introduction of the sheath.

The sheath 36 may be flexible and/or precurved to facilitate introduction and placement of the sheath tip 38 in the inguinal canal. Alternatively, the sheath may be actively deflectable with a radiopaque ringed soft tip. The sheath may include one or more lumens or passages to provide access to the inguinal canal and allow for the introduction of an optical visualization device, surgical tools and/or implantable prostheses for repairing the defect.

When the sheath 36 is placed in its desired position and the guidewire is no longer needed in the inguinal canal, the guidewire 34 may be removed from the sheath. A surgeon now has direct access to the inguinal canal through the sheath for reducing and/or repairing the hernia defect.

In one embodiment, a foam, gel or fluid, such as gas or liquid, may be injected through the sheath and into the inguinal canal to reduce the hernia. If desired, the reduction medium may be injected through the side arm of the sheath.

In one embodiment, a surgical tool may be introduced through the sheath to push the hernia from the inguinal canal. If desired, the tool may be introduced over the guidewire to reduce the hernia, prior to removing the guidewire from the sheath. The tool may include a surgical balloon, such as a round ball-type balloon, that pushes back the hernia sack as it is advanced along the guidewire.

In one embodiment, a surgeon may insert a finger through the sheath and reduce the contents of the inguinal canal.

It is to be appreciated that a surgeon may employ any one or a combination of these and/or other techniques to reduce the contents of the inguinal canal as should apparent to one of skill in the art.

Once the hernia has been reduced from the inguinal canal, the defect may be percutaneously repaired to prevent or minimize recurrence of the hernia. In one illustrative embodiment shown in FIG. 6, a prosthesis 42 may be introduced through the sheath 36 and into the inguinal canal 22. Once placed in the inguinal canal, the prosthesis 42 is advanced laterally along the canal 22 from the percutaneous access location 24 to the hernia defect 26. For an indirect inguinal hernia, the prosthesis is advanced to the inguinal ring 32.

Figure 7:
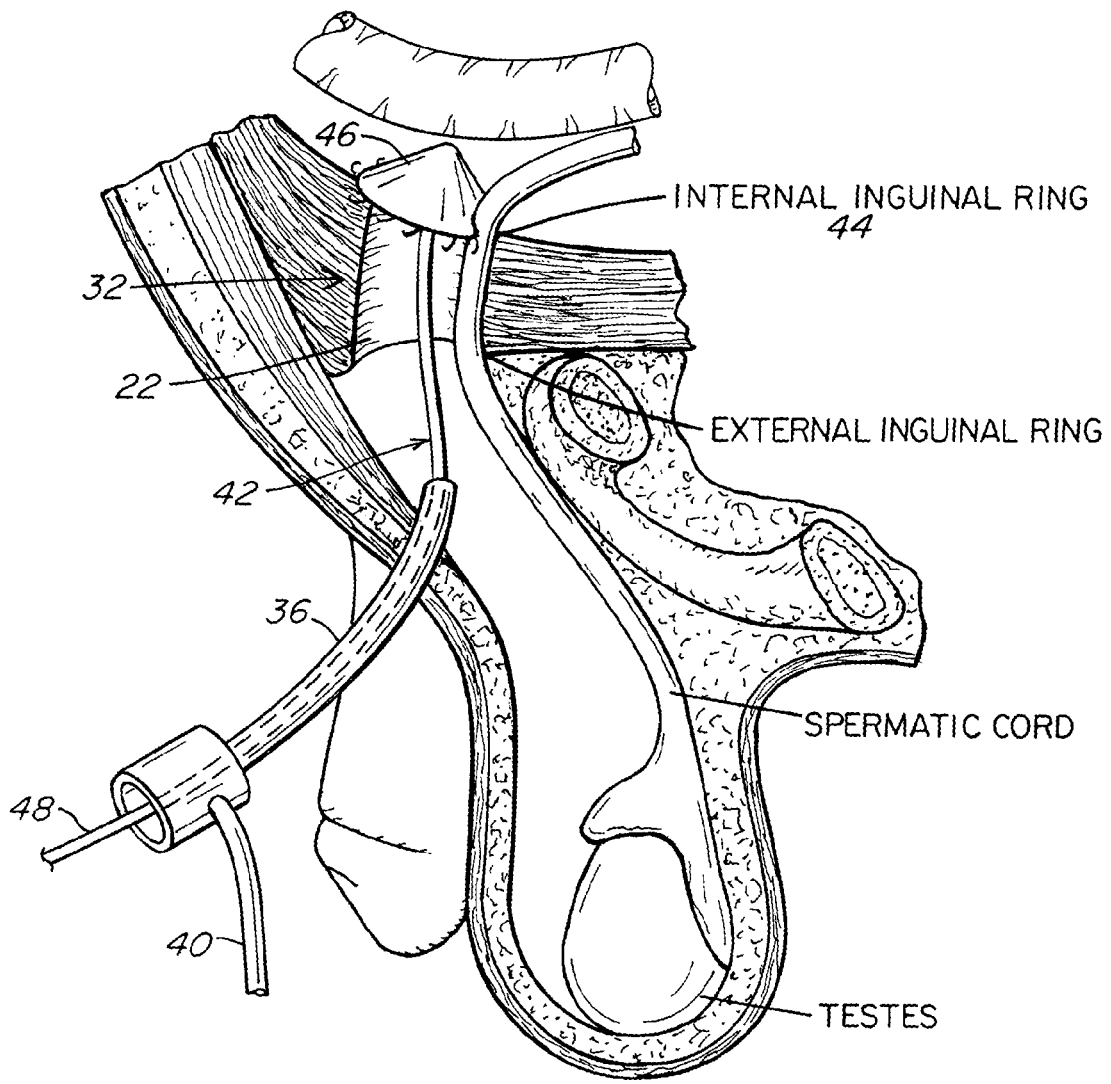

As illustrated in FIG. 7, advancement of the prosthesis 42 may continue through and beyond the internal inguinal ring 44. The prosthesis may thereafter be positioned to cover the defect. In one embodiment, the prosthesis 42 may include an expandable distal plug and/or patch 46 that is expandable to an enlarged deployed or open configuration after the plug or patch has been advanced beyond the defect. The expanded plug or patch 46 may thereafter be retracted or seated against the abdominal wall to cover or cap the internal inguinal ring.

Figure 8:
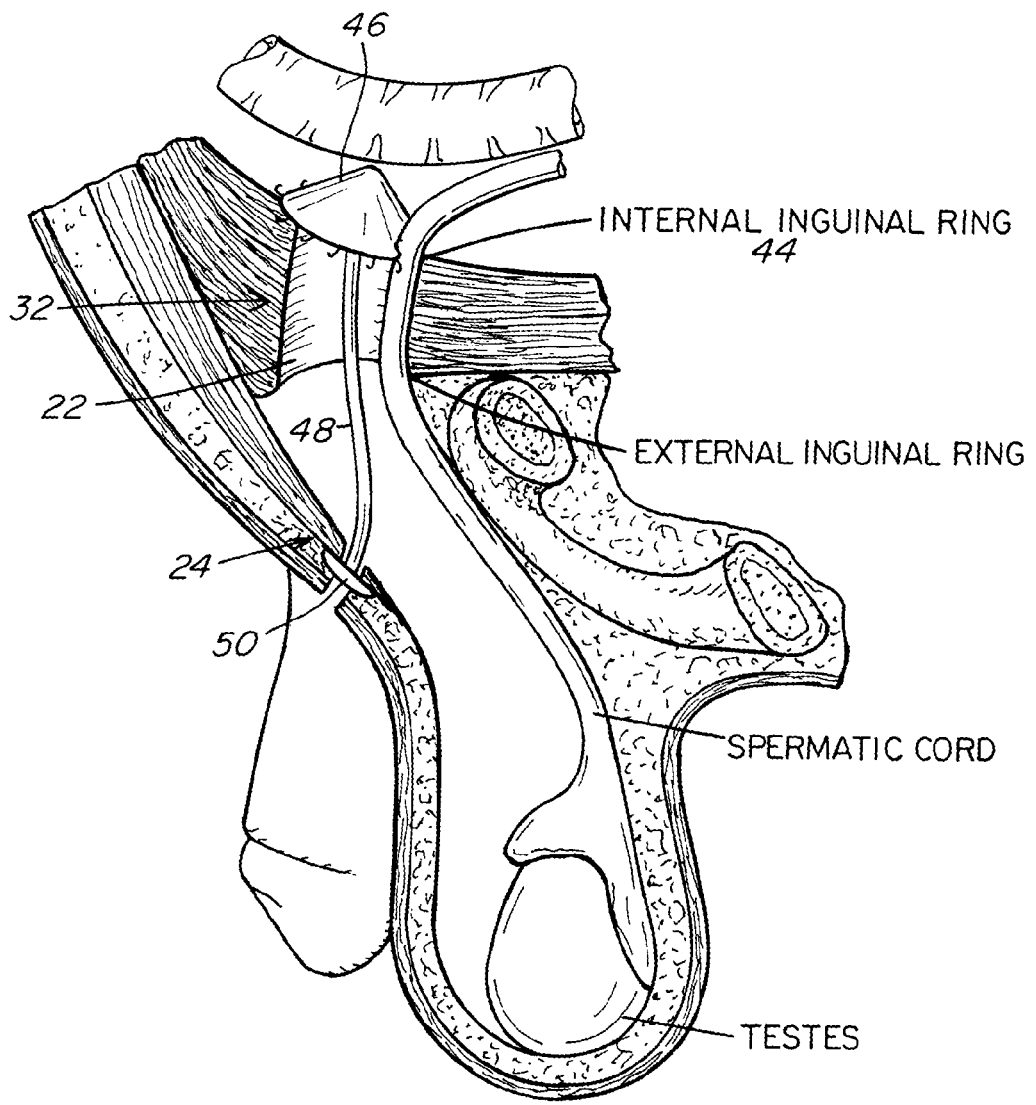

In one illustrative embodiment shown in FIGS. 7-8, the prosthesis 42 may include a cord or tether 48 that is attached to the distal plug or patch 46 to facilitate placement and anchoring of the plug or patch over the defect. As shown, the cord 48 may have a length sufficient to extend from the plug or patch 46 through the sheath 36 and outside the patient so that a surgeon may manipulate and pull the cord to retract and seat the plug or patch 46 against the abdominal wall.

Once the distal plug or patch 46 has been positioned and seated, it may be anchored proximally via the cord 48 to prevent the plug or patch from moving away from the inguinal ring. In one embodiment shown in FIG. 8, the prosthesis may include a proximal anchor 50 that is attached to a proximal end of the tether 48 which is placed under tension to maintain the distal plug or patch 46 in position against the defect. As shown, the anchor 50 may be positioned subcutaneously at the percutaneous entrance 24 to the inguinal canal after removal of the sheath.

The prosthesis may include a distal plug and/or patch 46 having a configuration suitable for covering and/or sealing the defect as should be apparent to one of skill in the art. In one embodiment, the prosthesis may include an umbrella-like patch that is collapsible into a slender configuration to facilitate introduction through the sheath and advancement along the inguinal canal and through the inguinal ring. The distal patch is expandable to an open or deployed configuration that has a shape and/or size that is sufficient to cap, cover or plug the defect.

Figure 9:
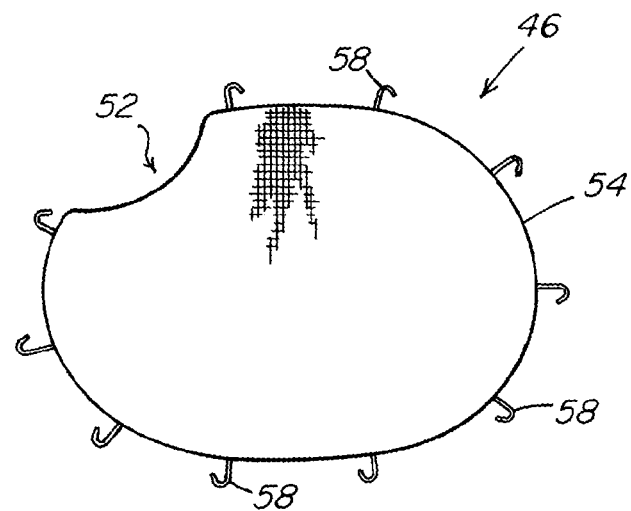
FIG. 9 is an illustration of a hernia repair patch according to one embodiment of the invention.
Figure 10:
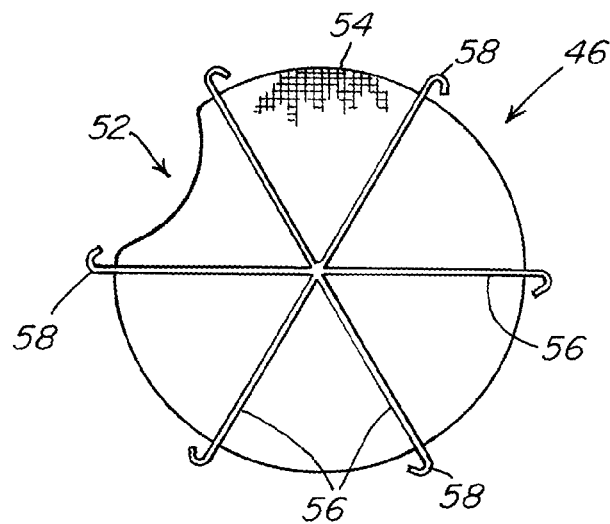
FIG. 10 is an illustration of a hernia repair patch according to another embodiment of the invention.

In illustrative embodiments shown in FIGS. 9-10, the patch 46 may have an oval or round shape. For some applications, it may be desirable to accommodate sensitive structures, such as inguinal nerves and/or the spermatic cord, occupying the inguinal space. As shown, the patch 46 may include an indentation, notch or other relief 52 along its periphery 54 that is configured to receive adjacent anatomical structure when the patch is positioned at the defect site. However, a relief is not required for all embodiments of the patch, and the patch may have any configuration or shape suitable for capping, covering or plugging the defect as should be apparent to one of skill in the art.

To facilitate deployment of the prosthesis, the patch 46 may include one or more support members that expand and/or support the patch in an open or deployed configuration. In one embodiment shown in FIG. 10, the patch 46 may include one or more arms, struts or spokes 56 that extend in an outward radial direction from the central region of the patch toward the outer periphery 54 of the patch. In this manner, the patch 46 may be provided with a frame-like structure to open and/or deploy the patch.

It is to be appreciated that the prosthesis may employ any suitable support member configuration as should be apparent to one of skill in the art. For example, the support members may include one or more resilient rings, such as concentric rings, to open or deploy the patch.

The support members 56 may be formed of a shape memory or superelastic material, such as nitinol, that allows the members to transform from a collapsed configuration to an expanded configuration to expand or open the patch. If desired, the support members may be formed of a radiopaque material to assist with introducing and guiding the prosthesis to the defect site. However, any suitable material as should be apparent to one of skill in the art may be used for the support members.

The patch may include one or more anchors to maintain and/or stabilize the patch at the defect site. In illustrative embodiments shown in FIGS. 9-10, the patch 46 may include a plurality of anchors 58 that are spaced about the patch to penetrate, grasp or grip tissue at the defect site. The anchors 58 may include hooks that are located about the periphery 54 of the patch. In one embodiment shown in FIG. 10, the anchors 58 may extend from the ends of the support members 56. It is to be appreciated that anchors are not required for each embodiment of the prosthesis, and that the anchors, if desired, may include any suitable configuration as should be apparent to one of skill in the art.

The prosthesis may include a proximal anchor 50 having any configuration apparent to one of skill in the art that is suitable for maintaining tension on the cord 48 to hold the distal patch 46 in position at the defect. In one embodiment, the prosthesis may include an anchor disc 50 that is secured to the proximal end of the tether 48. The anchor disc may be configured for subcutaneous placement in a patient. Other anchoring devices may include, but are not limited to, a hinged T-bar, a rollable button, a staple and a suture.

The distal patch, the tether and the proximal anchor may be formed of any biocompatible material suitable for hernia repair as should be apparent to one of skill in the art. The patch, tether and anchor may include absorbable, non-absorbable or a combination of absorbable and non-absorbable materials. In one embodiment, the patch may be formed of a collagen material that is resorbable over a predetermined period of time.

For some repair procedures, it may be desirable to introduce a biocompatible material, such as a foam, into the inguinal canal to reduce and/or repair the hernia defect. The foam may be used either alone or with an implantable prosthesis to repair the defect.

Figure 11:
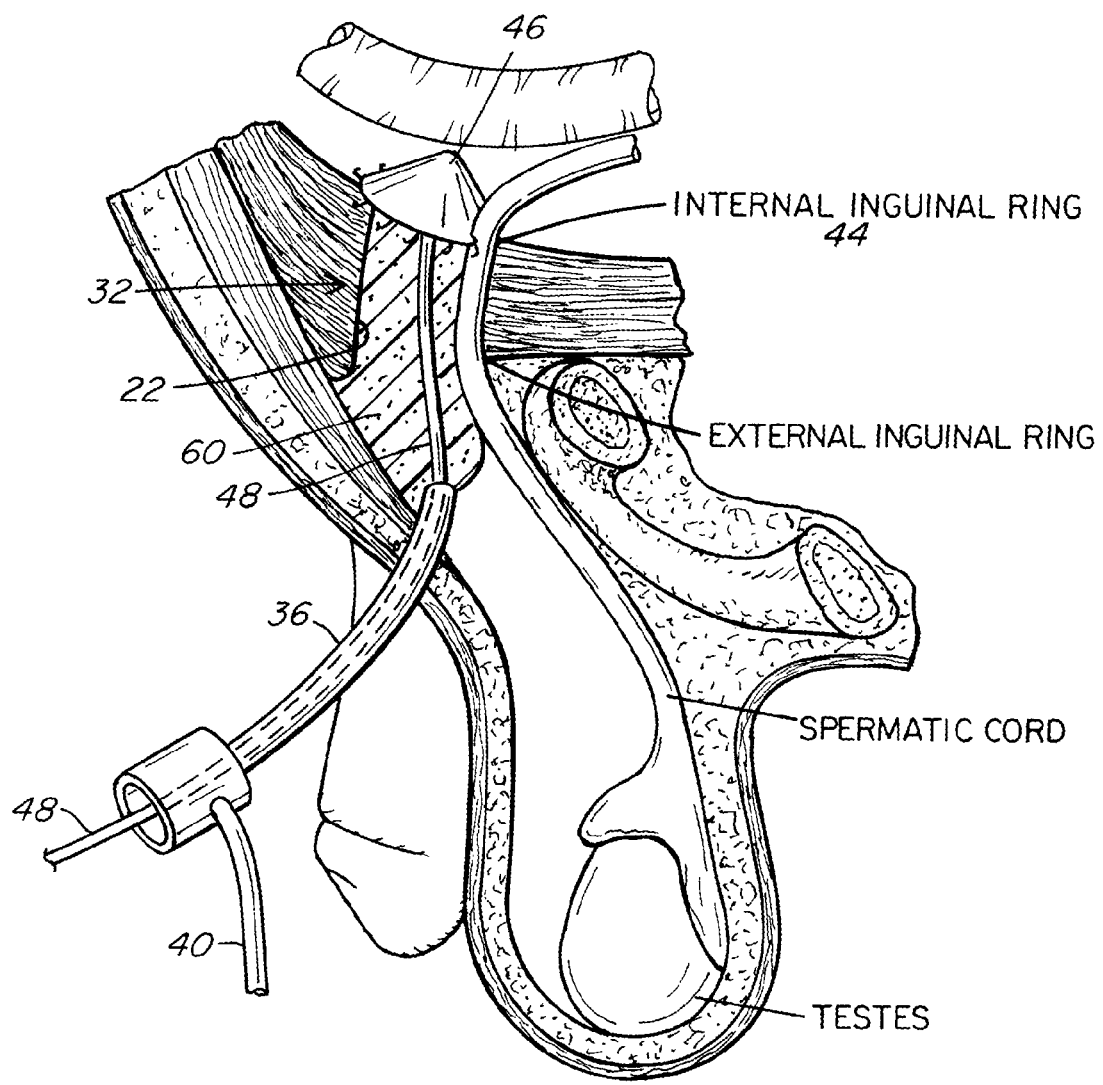
FIGS. 11-12 are schematic illustrations of a method of percutaneously repairing an inguinal hernia according to another embodiment of the invention.

In one illustrative embodiment shown in FIG. 11, a foam material 60 may be injected into the canal 22 through the sheath 36. For an indirect inguinal hernia, the foam 60 may be injected until the canal is filled to the internal inguinal ring 44. The foam 60 may be capped distal to the internal inguinal ring using either a permanent or temporary cap or patch 46.

As illustrated, the foam 60 may be introduced into the inguinal canal 22 after a distal patch 46 has been positioned over the internal inguinal ring 44, such as in a manner described above. The distal patch 46 may be held in position over the inguinal ring using a tether 48 as the foam is being introduced into the canal.

Figure 12:
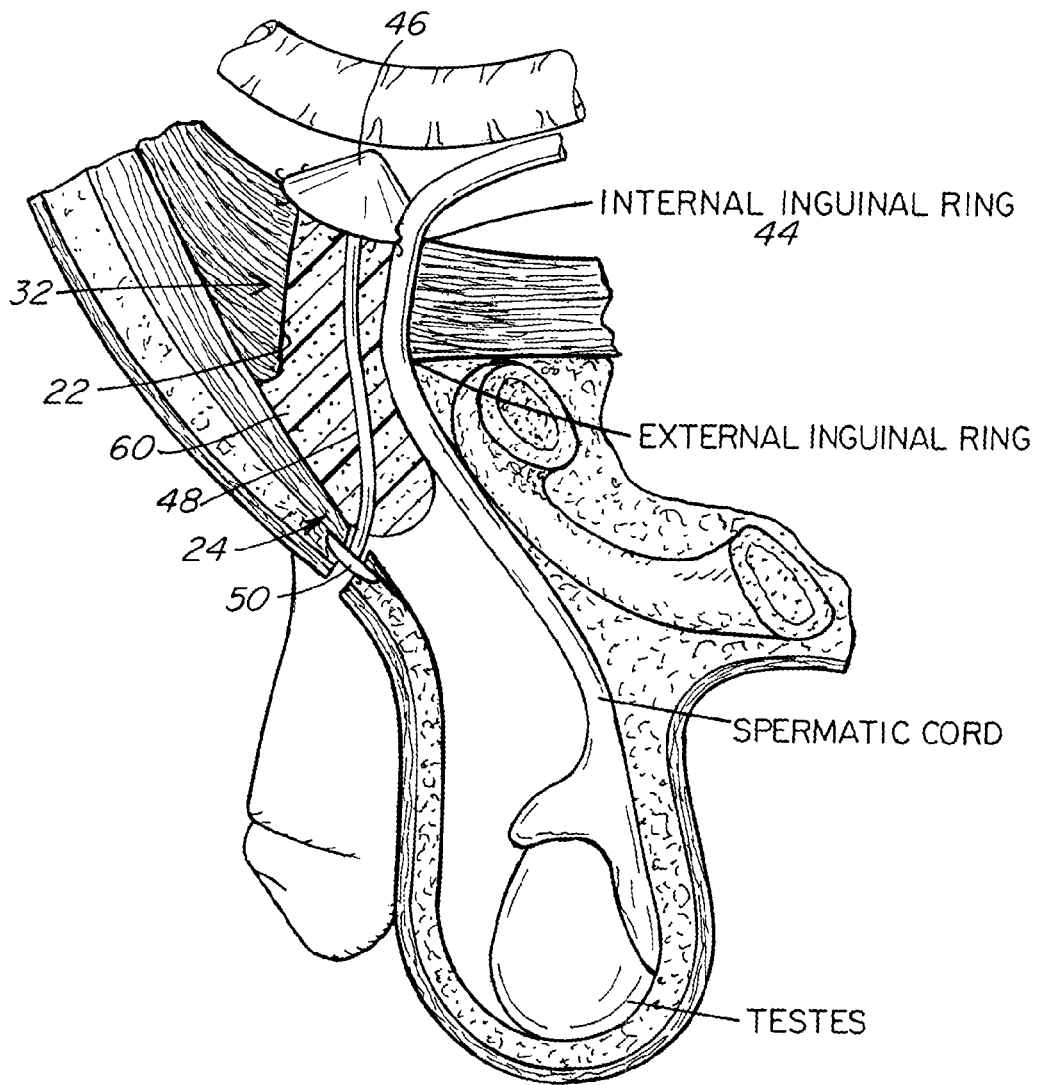

As illustrated in FIG. 12, the distal patch 46 may be anchored in position using a proximal anchor 50 that is attached to a proximal end of the tether 48 which is placed under tension to maintain the distal plug or patch in position against the defect. The anchor 50 may be attached to the tether 48 and positioned subcutaneously, as shown, at the percutaneous entrance 24 to the inguinal canal after introduction of the foam and removal of the sheath. As shown, the foam 60 is located between the patch 46 and the anchor 50. However, if desired, the foam may be capped using only a distal patch that is positioned over the internal inguinal ring.

The foam 60 may permanently or temporarily fill the canal 22 to prevent abdominal viscera from reentering the canal. The foam may solidify to fill the three-dimensional shape of the canal and thereby resist upward migration into the abdomen. The foam may be formed of any suitable non-absorbable material or absorbable material, such as collagen, as should be apparent to one of skill in the art. If desired, the foam may be formed of a radiopaque material.

In one embodiment, the foam may be injected into and contained within a rolling membrane, such as a compliant sliding balloon. The membrane may be formed of any suitable non-absorbable material or absorbable material, such as collagen, as should be apparent to one of skill in the art.

It should be understood that the foregoing description of various embodiments of the invention are intended merely to be illustrative thereof and that other embodiments, modifications, and equivalents of the invention are within the scope of the invention recited in the claims appended hereto. Further, the methods and prostheses described above include various aspects and/or features that may be employed singularly or in any suitable combination.

What is claimed is:

1. A method of percutaneously repairing an inguinal hernia defect, the method comprising acts of: (a) percutaneously accessing an inguinal canal of a patient; (b) percutaneously delivering a biocompatible foam material into the inguinal canal; and (c) percutaneously plugging and/or covering the hernia defect with an implantable prosthesis including a patch having a tether extending therefrom, the patch being collapsible into a slender configuration for percutaneous delivery into and advancement along the inguinal canal.

2. The method according to claim 1, wherein act (b) includes filling the inguinal canal with the foam material from the location of percutaneous access toward the hernia defect.

3. The method according to claim 2, wherein act (b) includes filling the inguinal canal to an inguinal ring.

4. The method according to claim 1, wherein the foam material solidifies in the shape of the inguinal canal.

5. The method according to claim 1, wherein act (c) occurs prior to act (b).

6. The method according to claim 1, wherein act (c) includes percutaneously delivering the prosthesis into the inguinal canal, and advancing the prosthesis along the inguinal canal from the location of percutaneous access toward the hernia defect.

7. The method according to claim 6, wherein act (c) includes advancing the prosthesis through the hernia defect.

8. The method according to claim 6, wherein act (c) includes collapsing the prosthesis to a first configuration for delivering and advancing the prosthesis, and expanding the prosthesis to a second configuration that is larger than the first configuration to plug and/or cover the hernia defect.

9. The method according to claim 1, wherein act (c) includes placing the prosthesis against a distal side of the hernia defect.

10. The method according to claim 1 wherein act (c) further includes tensioning the tether to draw the patch over the hernia defect.

11. The method according to claim 1, wherein act (c) includes anchoring the tether to maintain the patch in position over the hernia defect.

12. The method according to claim 1, wherein the prosthesis includes a proximal anchor, and wherein act (c) includes attaching the tether to the proximal anchor.

13. The method according to claim 12, wherein the proximal anchor is subcutaneously located proximate the percutaneous access.

14. The method according to claim 1, wherein the hernia defect is an indirect inguinal hernia, and wherein act (c) includes placing the prosthesis over the inguinal ring.

15. The method according to claim 1, wherein act (a) includes establishing percutaneous access to the inguinal canal using a Seldinger-like procedure.

* * * * *